US006319501B1

(12) United States Patent
Neurath et al.

(10) Patent No.: US 6,319,501 B1
(45) Date of Patent: Nov. 20, 2001

(54) METHOD OF IMMUNIZING AGAINST HEPATITIS B VIRUS

(75) Inventors: Alexander Robert Neurath; Nathan Strick, both of New York; Yasmin M. Thanavala; Michael W. Pride, both of Buffalo, all of NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 08/150,776

(22) Filed: Nov. 12, 1993

Related U.S. Application Data

(63) Continuation of application No. 08/001,422, filed on Jan. 6, 1993, now abandoned, which is a continuation of application No. 07/759,985, filed on Sep. 13, 1991, now abandoned, which is a continuation of application No. 07/555,555, filed on Jul. 19, 1990, now abandoned.

(51) Int. Cl.⁷ ............................. A61K 39/29; C07K 14/02
(52) U.S. Cl. ...................................... 424/189.1; 424/227.1
(58) Field of Search .................................. 424/89, 189.1, 424/227.1

(56) References Cited

U.S. PATENT DOCUMENTS

| | | | |
|---|---|---|---|
| 4,778,761 | * 10/1988 | Miyanohara et al. | 435/320.1 |
| 4,803,164 | * 2/1989 | Hitzeman et al. | 435/69.1 |
| 5,017,558 | * 5/1991 | Vyas | 514/14 |

OTHER PUBLICATIONS

Okamoto et al. (1989) Mol. Immunol. 26(2), 197–205.*
Brown et al. (1984) J. Immunol. Meth. 72, 41–48.*
Brown et al, Abstract, Lancet 2, 184–187 (1984).*
Lai et al., Abstract, Blood, 73(1), 17–19 (1989).*
Wands et al. Proc. Natl. Acad.Sci, U.S.A., vol. 83, pp 6608–6612, Sep. 1986, Medical Sciences "Identification of Transmission of Hepatitis B..".
Coursage et al. The Lancet, Dec. 12, 1987, "HBsAG Positive Reactivity in Man Not Due to Hepatitis B Virus". pp 1354–1358.
Neurath et al. Peptide Research, vol. 3, No. 3 (1990), pp 116–122, "Toleration of Amino Acid Substitutins Within Hepatitis B Virus . . . ".
Lai et al. Blood, vol. 73, No. 1 (Jan.), 1989; pp. 17–19, "Hepatitis B Virus DNA in the Serum of Sardinian Blood Donors . . . ".
Carman et al. The Lancet, vol. 336, p. 325–329, (1990) "Vaccine–Induced Escape Mutant of Hepatitis B Virus".
Current Protocols in Molecular Biology, vol. 1, Supplement 6.
Journal of Virology, May 1988, p. 1836–1839, vol. 62, No. 5.
Recombinant DNA, A short Course, Chapter 8, In Vitro Mutagenesis, pp. 106–116.
J. Mol. Biol. (1987) 195, 343–350, "Insertions in the Hepatitis B Surface Antigen".
Immunochemistry of viruses, The basis for serodiagnosis and vaccines, Antigenic structure of foot–and–mouth disease virus, pp. 274–276.

* cited by examiner

Primary Examiner—Robert A. Schwartzman
(74) Attorney, Agent, or Firm—Michael L. Dunn

(57) ABSTRACT

A method for immunizing a human against hepatitis B virus comprising administering to the human a vaccine comprising a hepatitis B virus surface antigen, wherein included in the vaccine is one or more antigens of non-permitted variant sequences within residues S(139–147) of the hepatitis B virus surface antigen.

2 Claims, 5 Drawing Sheets

METHOD OF IMMUNIZING AGAINST HEPATITIS B VIRUS

This is a File Wrapper Continuation of application Ser. No. 08/001,422, filed Jan. 6, 1993, abandoned, which in turn is a continuation of application Ser. No. 07/759,985, filed Sep. 13, 1991, abandoned, which in turn is a continuation of application Ser. No. 07/555,555, filed July 19, 1990 abandoned.

GOVERNMENT RIGHTS

This invention was made with United States government support under Grant RO1 AI27976 from the NIH. The United States government has certain rights in this invention.

BACKGROUND OF THE INVENTION

1. Field of the Invention

The present invention concerns an improved method for immunizing against hepatitis B virus (HBV) by including in a hepatitis B virus vaccine one or more antigens of non-permitted variant sequences within residues S(139–147) of the hepatitis B virus surface antigen.

2. Background Information

There are approximately 600,000 persistent carriers of hepatitis B virus (HBV) in the United States; the estimated total number of carriers in the world is 300 million. A considerable portion of HBV carriers have chronic liver disease. The involvement of HBV in liver cancer has been demonstrated (W. Szmuness, Prog. Med. Virol. 24, 40 (1978) and R. P. Beasley, L.-Y. Hwang, C. -C. Ling, C.-S. Chien, Lancet, Nov., 21, 1129 (1981)).

HBV infections thus represent a major public health problem worldwide. Already available vaccines (S. Krugman, in Viral Hepatitis: Laboratory and Clinical Science, F. Dienhardt, J. Dienhardt, Eds. Marcel Dekker, Inc., New York-Basel, 1983, pp. 257–263) produced from the serum of HBV carriers, because of limited resources and production costs involved, do not provide the appropriate means to control and eradicate the disease worldwide. There is hope, however, that this may be accomplished by vaccines based on recombinant DNA technology and/or synthetic peptides.

The biology, structure and immunochemistry of HBV and the genetic organization of its DNA genome have been reviewed (B. S. Blumberg, Science, 197, 17, (1977)). The cloning and sequencing of the genome of several hepatitis virus (HBV) isolates led to the elucidation of the genetic structure of the viral DNA (P. Tiollais, P. Charnay, G. N. Vyas, Science, 213, 406, (1981)).

The immunologic markers of HBV infection include the surface antigen (HBsAg), the core antigen (HBcAg), the "e" antigen (HBeAg) and their respective antibodies. Antibodies against HBsAg are protective against HBV infection.

Several antigenic subtypes of HBV and of subviral approximately 22 nm diameter particles (hepatitis B surface antigen; HBsAg) have been recognized (G. Le Bouvier, A. Williams, Am. J. Med. Sci., 270,.165 (1975)). All of these subtypes (for example, ayw, adyw, adw2, adw and adr) share common (group-specific) envelope epitopes, the immune response against which appears sufficient for protection against infection by any of the virus subtypes (W. Szmuness, C. E. Stevens, E. J. Hartley, E. A. Zang, H. J. Alter, P. E. Taylor, A. DeVera, G. T. S. Chen, A. Kellner et al, N. Enql. J. Med., 307, 1481, (1982)).

Since dominant B-cell epitopes on the S-protein of the hepatitis B virus surface antigen (HBsAg) are discontinuous, it has proved difficult to mimic them by linear synthetic peptides. However, some cyclic peptides derived from segments of the hepatitis B virus surface antigen sequence were shown to bind anti-HBs.

A cyclic peptide corresponding to the sequence S(139–147), derived from the sequence of the S-protein subtype adw, with a disulfide bond between residues (139–147) was reported to bind anti-HBs with an affinity similar to that determined for the reaction between native HBsAg and anti-HBs (S. E. Brown, C. R. Howard, A. J. Zuckerman and M. W. Steward, 1984, "Determination of the Affinity of Antibodies to Hepatitis B Surface Antigen in Human Sera", J. Immunol. Methods, 72:41–48; S. E. Brown, A. J. Zuckerman, C. R. Howard and M. W. Stewart, 1984, "Affinity of Antibody Responses in Man to Hepatitis B Vaccine Determined With Synthetic Peptides", Lancet, 2:184–187. The same peptide after polymerization with glutaraldehyde, elicited antibodies reactive with native HBsAg (C. R. Howard, J. Allan, S. -H. Chen, S. E. Brown and M. H. Steward, 1986, "Progress Toward a Synthetic Hepatitis B Vaccine", pp. 133–136. In H. Peeters (Ed), Protides of the Biological Fluids: Proceedings of the Thirty-Fourth Colloquium, Pergamon Press, Oxford, England). These results indicate that the sequence S(139–147) is a portion of a dominant discontinuous B-cell epitope of the S-protein.

The peptide S(139–147) in both linear and cyclic forms elicited the proliferation of T-helper ($T_h$) lymphocytes from mice and humans immunized with HBsAg (Neurath, A. R. and Y. Thanavala, 1990 supra. These results indicate that the S(139–147) segment of S-protein is part of an immunologically important region recognized by both B and $T_h$ cells.

Since the S(139–147) segment of the S-protein sequence is important for eliciting HBsAg-specific B and $T_h$-cell responses, amino acid replacements within this sequence may profoundly affect the recognition of the S-protein by both B- and $T_h$-cells and the specificity of immune responses to the S-protein. Among well-defined serological-subtypes of HBsAg there is a single amino acid substitution (serine threonine) at residue 143. All other amino acid residues within this sequence are completely conserved among the distinct HBV subtypes.

Evidence for the existence of genetic variants of HBV with envelope protein epitopes distinct from those present on already defined HBV subtypes has been reported recently M. E. Lai, P. Farci, A. Figus, A. Balestrieri, M. Arnone and G. N. Vyas, 1989, "Hepatitis B Virus DNA in the Serum of Sardinian Blood Donors Negative for the Hepatitis B Surface Antigen", Blood, 73:17–19. Direct evidence for the emergence of such variants under immunological pressure in vivo comes from recent studies of McMahon et al (G. McMahon, L. A. McCarthy, D. Dottavio and L. Ostberg, not yet published "Surface Antigen and Polymerase Gene Variation in Hepatitis B Virus Isolates from a Monoclonal Antibody Treated Liver Transplant Patient", B. Hollinger (Ed), Proceedings of the 1990 International Symposium on Viral Hepatitis and Liver Disease, Wiley, N.Y., U.S.A.).

Amino acid replacements within the S-protein sequence may lead to a loss of subtype specific determinants d/y or w/r (H. Okamoto, S. Omi, Y. Wang, Y. Itoh, F. Tsuda, T. Tanaka, Y. Akahane, Y. Miyakawa and M. Mayumi, 1989, "The Loss of Subtypic Determinants in Alleles, d/y or w/r, on Hepatitis B Surface Antigen", Mol. Immunol., 26:197–205). However, these newly discerned HBV subtypes, which are nonreactive with subtype specific reagents developed earlier, still contain the group specific "a" determinants considered essential for eliciting protective immunity (Neurath, 1989, "Chemical Synthesis of Hepatitis B Vaccines", p. 210–242, In A. J. Zuckerman (Ed), *Recent Developments in Prophylactic Immunization,* Kluwer Academic Publishers, Dordrecht, The Netherlands; Neurath and Thanavala, 1990, "Hepadnaviruses", In M. H. V. Van Regenmortel and A. R. Neurath (Eds), *Immunochemistry of Viruses II,* Elsevier Science Publishers, Amsterdam, The Netherlands, in press). However, HBV variants may have altered or insufficiently cross-reactive a determinants recognizable by antibodies and T cells elicited as a result of immunization with defined subtypes of HBV. Such variants may possibly cause infections not preventable by current hepatitis B vaccines. For this reason, it is important to define amino acid replacements within dominant group-specific B and T cell epitopes which would lead to the generation of escape mutants.

Antigenic variation with respect to foot-and-mouth disease virus is discussed in *Immunochemistry of Viruses. The Basis for Serodiagnosis and Vaccines,* Ed. M. H. V. Van Regenmortel and A. R. Neurath, "Antigenic Structure of Foot-And-Mouth Disease Virus", F. Brown, 274–276, (1985).

| DEFINITIONS | | |
|---|---|---|
| Amino Acid | 3-letter code | 1-letter code |
| Alanine | Ala | A |
| Arginine | Arg | R |
| Asparagine | Asn | N |
| Aspartic acid | Asp | D |
| Cysteine | Cys | C |
| Glutainine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

SUMMARY OF THE INVENTION

The present invention concerns an improved method for immunizing against hepatitis B virus comprising administering to a human a vaccine containing a hepatitis B virus surface antigen, e.g., the entire hepatitis B virus S protein or one or more portions of the entire S protein, wherein the improvement comprises including in such vaccine one or more antigens of non-permitted (not tolerated) variant sequences within residues S(139–147) (CTKPSDGNC) of the hepatitis B virus surface antigen. The antigen may be the entire S protein sequence or one or more portions thereof. Such antigen will contain one or more replacements within residues S(139–147).

The present invention is also directed to a method for overcoming the detrimental immunological effects of mutations in the S(139–147) sequence of hepatitis B virus surface antigen comprising including in an immunogenic hepatitis B vaccine for administration to a human one or more antigens of non-permitted variant sequences within residues S(139–147) of the hepatitis B virus surface The present invention also relates to an improved hepatitis B virus vaccine, comprising adding to the vaccine (containing either the entire hepatitis B virus S protein or one or more portions thereof) one or more antigens of non-permitted variant sequences within residues S(139–147) of the hepatitis B virus surface antigen.

More particularly, the above described inventive methods and vaccines involve the utilization of a non-permitted variant sequence with an amino acid replacement at one or more of positions 142, 143, 144, 145 or 146 of S(139–147). Still more particularly, the inventive methods and vaccines involve the employment of a non-permitted variant sequence with one or more of the following amino acid replacements:

| | |
|---|---|
| 142 | P to S, |
| 143 | T(S) to M, |
| 144 | D to N or E, |
| 145 | G to A or R, or |
| 146 | N to D. |

BRIEF DESCRIPTION OF THE DRAWINGS

For the purpose of illustrating the invention there is shown in the drawings forms which are presently preferred. It is to be understood, however, that the present invention is not limited to the precise arrangements and instrumentalities depicted in the drawings.

DETAILED DESCRIPTION OF THE DRAWINGS

Figure 1:
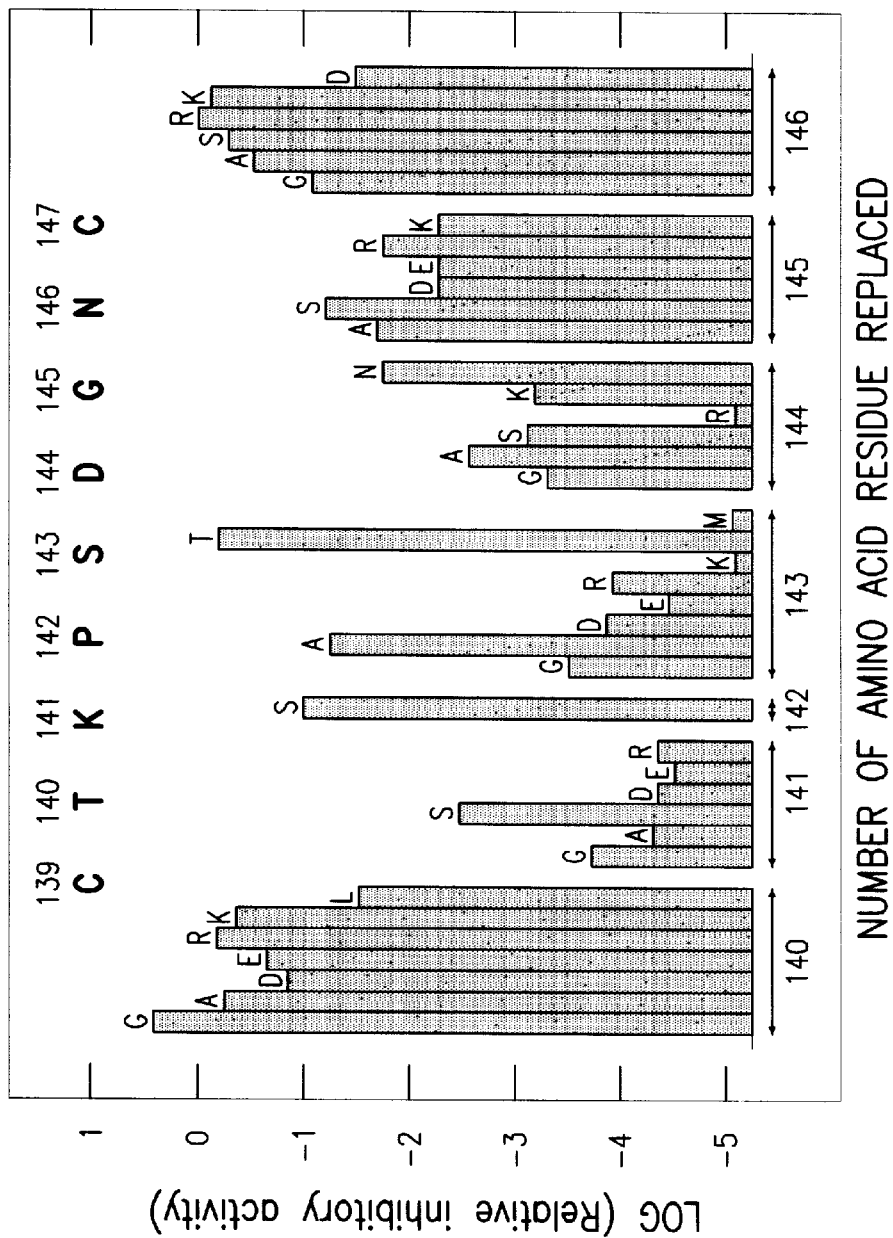
FIG. 1 is a series of bar graphs depicting the relative inhibitory activity of replacement set peptides on the reaction of antibodies recognizing the (139–147) segment of the S-protein of hepatitis B virus surface antigen (HBsAg) with HBsAg.

FIG. 1. concerns the relative inhibitory activity of replacement set peptides on the reaction of antibodies recognizing the (139–147) segment of the S-protein with HBsAg. The concentration of each peptide at which the attachment of antibodies to solid phase HBsAg was reduced by 50% ($C_{50}$) was determined. $C_{50}$ of the parent peptide (sequence shown on top of the bars) was divided by $C_{50}$ for each inhibitory peptide and the $\log_{10}$ of the ratio was plotted on the ordinate. Amino acid residues replacing amino acids in the parent sequence are shown on the top of each bar. The sequence numbers of residues being replaced in the parent sequence are shown on the bottom of the bar groups.

Figure 2:
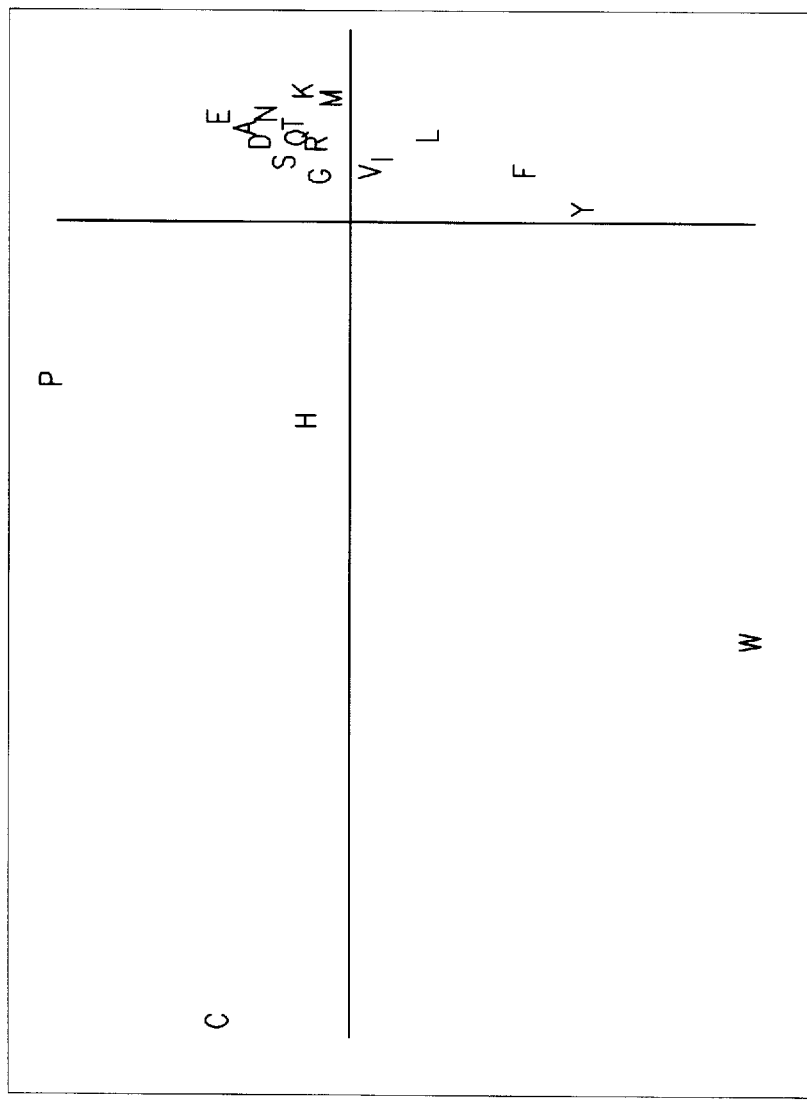
FIG. 2 is an Euclidean representation of an amino acid distance matrix for alignment of structurally related proteins.

FIG. 2 is an Euclidean representation of an amino acid distance matrix for alignment of structurally related proteins (Risler et al, *Journal of Molecular Biology,* 1988, Vol. 204, pp. 1019–1029).

Figure 3:
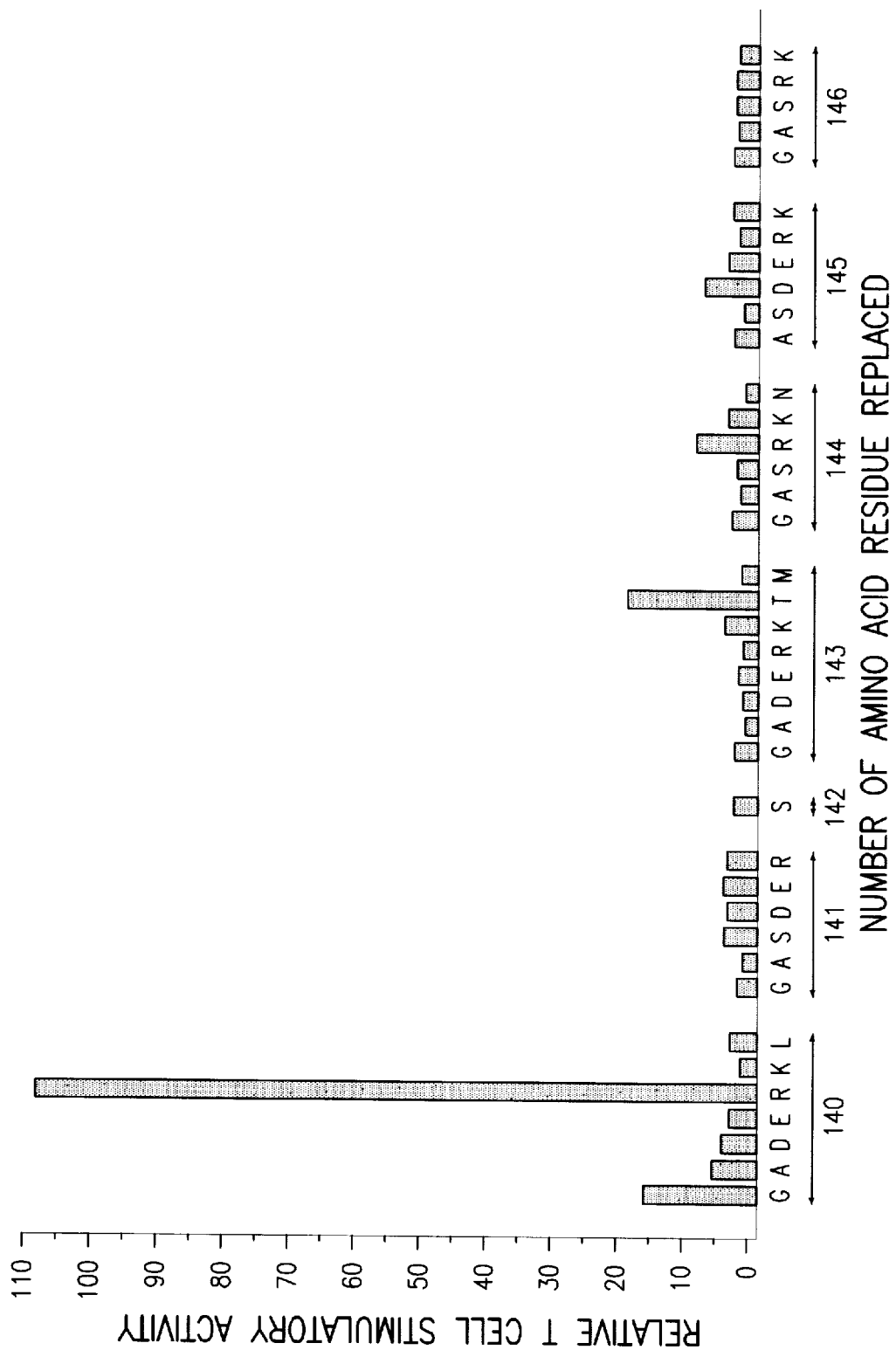
FIGS. 3 and 4 are bar graphs depicting relative T cell-stimulatory activity of replacement set peptides on T-cells from mice immunized with HBsAg, expressed as a percentage of stimulation elicited by the parent peptide.

FIG. 3. depicts relative T cell-stimulatory activity of replacement set peptides expressed as a percentage of stimulation elicited by the parent peptide. Murine T cells were obtained by nylon wool column purification of Balb/c lymph node cells primed with HBsAg, subtype ayr (Scripps Laboratories, San Diego, Calif.). For comparison, the T cell-stimulatory response to rHBsAg, subtype ad(32,657), HBsAg subtype ayr (54,640), parent peptide (16,073=100%) and media control (330) were examined at optimal concentrations for each antigen. Values shown in parentheses are mean cpms corresponding to $^3$H-TdR incorporation measured in triplicate. Amino acid residues replacing amino acids in the parent sequence are shown at the bottom of the bars.

Figure 4:
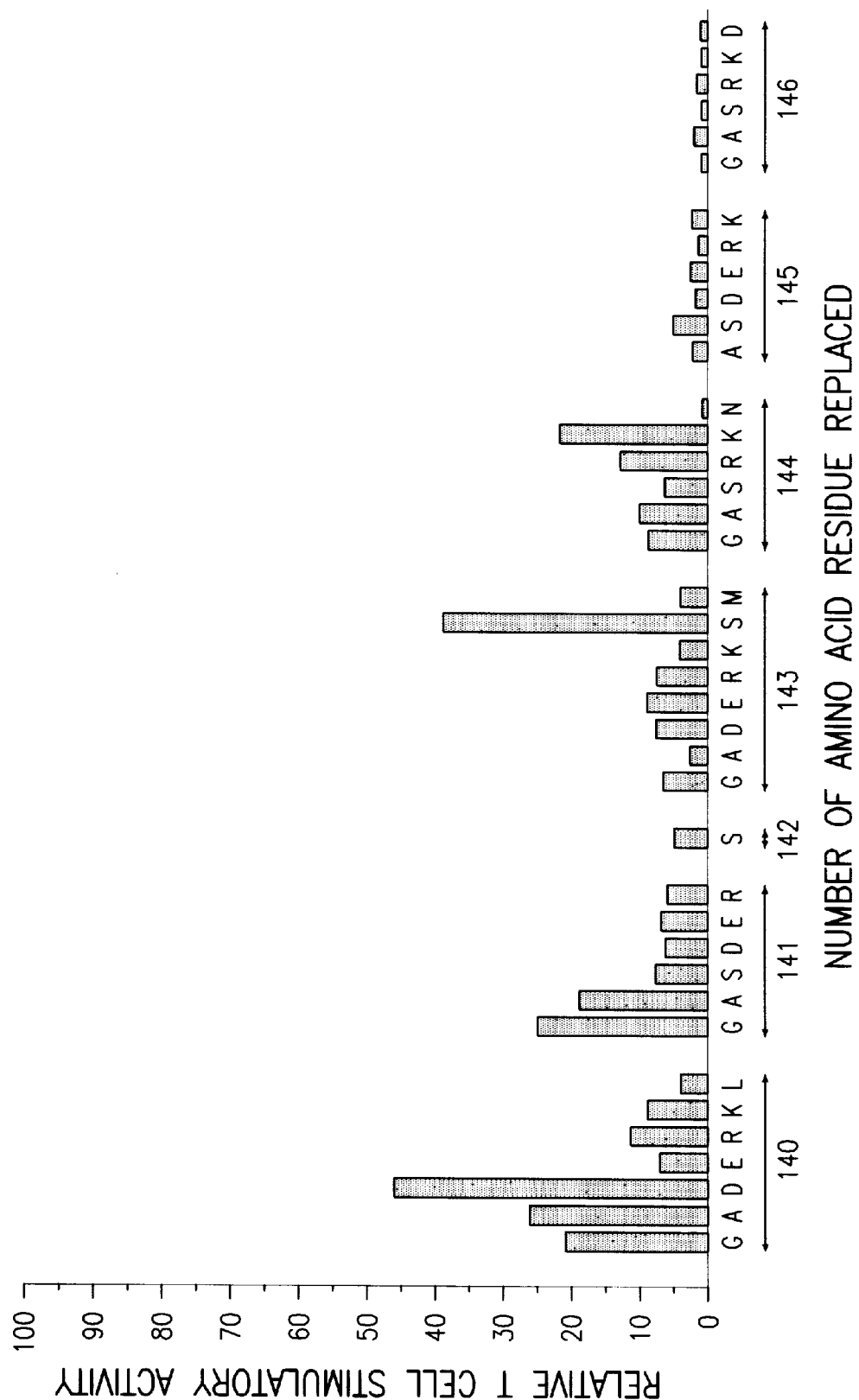

FIG. 4. depicts relative T cell-stimulatory activity of replacement set peptides expressed as a percentage of stimulation elicited by the parent peptide. Murine T cells were obtained by nylon wool column purification of Balb/c lymph node cells primed to rHBsAg, subtype ad (RecombiVax HB, Merck Sharp & Dohme). For comparison the T cells-stimulatory response to rHBsAg, subtype ad (97,024), rHBsAg subtype ayr (64,878), parent peptide (44,916=100%) and media control (1,873) was examined at optimal concentrations for each antigen. Values shown in parentheses are mean cpms corresponding to $^3$H-TdR incorporation measured in triplicate. Amino acid residues replacing amino acids in the parent sequence are shown at the bottom of the bars.

Figure 5:
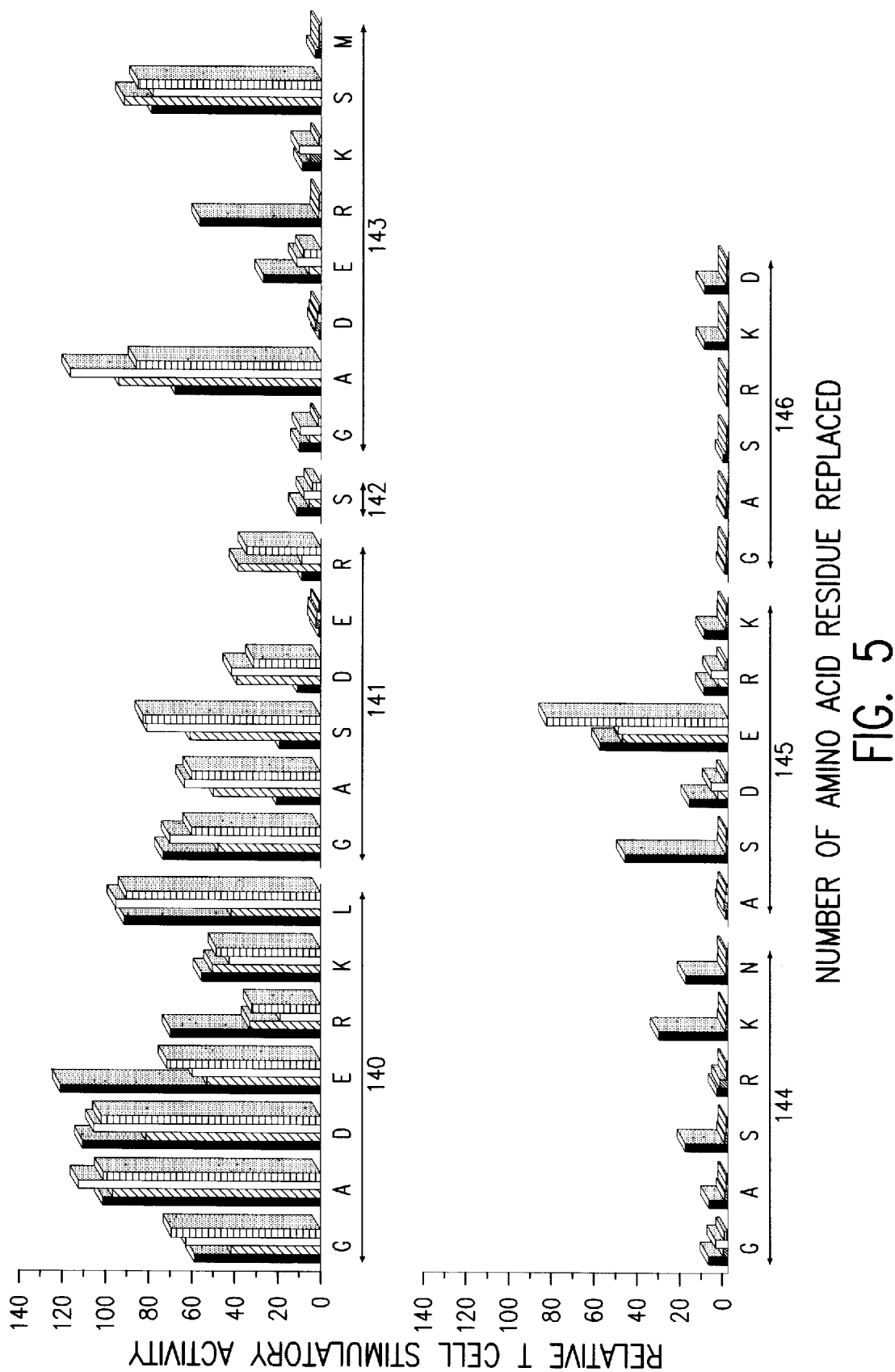
FIG. 5 are bar graphs depicting relative stimulatory activity on T-cells of humans vaccinated against hepatitis B of replacement set peptides expressed as a percentage of stimulation elicited by the parent peptide.

FIG. 5. shows relative stimulatory activity of replacement set peptides expressed as a percentage of stimulation elicited by the parent peptide. Human peripheral blood mononuclear cells (PBMC) were obtained from volunteers who had received the full course of the rHBsAg vaccine (Merck Sharp & Dohme). Donor 1 ■ Donor 2 z1 Donor 3 □ Donor 4 z2 For comparison average T cell-stimulatory response to rHBsAg subtype ad (146,478), parent peptide (96,930= 100%) and media control (1,147) was examined at optimal concentrations for each antigen. Values expressed in parentheses are mean cpms of $^3$H-TdR incorporation of triplicate wells. Amino acid residues replacing amino acids in the parent sequence are shown at the bottom of the bars.

DETAILED DESCRIPTION OF THE INVENTION

The amino acid sequence of the S(139–147) region of the S-protein corresponding to distinct subtypes of HBV (namely, ayw, adw$_2$, adw, adr, ayr and adyw) and to woodchuck and ground squirrel hepatitis B viruses (respectively, WHV and GSHV) is given hereinbelow in Table I. Sequence numbers corresponding to the S-protein of HBV are given on the top of Table I. Sequences corresponding to WHV and GSHV, respectively, were aligned with the HBV S-protein sequence.

TABLE I

| HBV | 139 | 140 | 141 | 142 | 143 | 144 | 145 | 146 | 147 |
|---|---|---|---|---|---|---|---|---|---|
| ayw | C | T | K | P | S | D | G | N | C |
| adw2 | C | T | K | P | T | D | G | N | C |
| adw | C | T | K | P | T | D | G | N | C |
| adr | C | T | K | P | S | D | G | N | C |
| ayr | C | T | K | P | S | D | G | N | C |
| adyw | C | T | K | P | S | D | G | N | C |
| WHV | C | L | K | P | T | A | G | N | C |
| GSHV | C | L | K | P | T | A | G | N | C |

Using a replacement set of peptides related to the S(139–147) segment of the HBV S-protein ("the parent peptide"), applicants studied the immunological effects of amino acid replacements. Non-permitted replacements were defined as those having less than 10% crossreactivity with the parent peptide at either the B cell or T cell level. By distinguishing experimentally between permitted (immunologically tolerated) replacements and non-permitted (not immunologically tolerated) replacements, applicants were able to discern the non-permitted replacements. Such non-permitted replacements signal the need for inclusion of mutant proteins in a vaccine.

Predicted amino acid similarities based on either of several algorithms (Van Regenmortel, M. H. V. and G. Daney de Marcillac, 1988, "An Assessment of Prediction Methods for Locating Continuous Epitopes in Proteins", *Immunology Letters,* 17:95–108) failed to discriminate between critical and tolerated replacements revealed herein (FIG. 1). Analogous replacements were permissible at one position of the S(139–147) sequence, while at another position they caused a drastic decrease in antigenicity (for example, compare the effect of K→PR replacements at position 146 and 141). This is consistent with the conclusion that B cell epitopes are comprised of both essential residues with limited replaceability and of nonessential residues which can be replaced by other amino acids (E. D. Getzoff, J. A. Tainer, R. A. Lerner and H. M. Geysen, 1988, "The Chemistry and Mechanism of Antibody Binding to Protein Antigens", p. 1–98; F. J. Dixon (Ed), *Advances in Immunology,* Academic Press, Inc., San Diego, Calif., U.S.A.).

Among others as depicted in FIG. 1, amino acid replacements were made within the S(139–147) sequence as depicted below in Table II Table II. Amino Acid Replacement Within the S (139–147) Region of S-protein Detected in Rare Serological Subtypes and Variants of HBV

| Residue Number | Amino Acid Replacement | Literature Reference |
|---|---|---|
| 142 | P→S | McMahon et al, supra |
| 143 | T(S)→M | McMahon et al, supra |
| 144 | D→N | McMahon et al, supra |
| 144 | D→E | Okainoto et al, 1989, Mol.Immunol., 26, 197–205 |
| 145 | G→A | Okainoto et al, 1989, supra |
| 145 | G→R | McMahon et al, supra |
| 146 | N→D | McMahon et al, supra |

Antigens for use in the present invention may have one or more of the following replacements in the S(139–147) sequence:

(a) T at residue position 140 is replaced by an amino acid other than G, D, E, R or K, (b) K at residue position 141 is replaced by any other amino acid, (c) P at residue position 142 is replaced by any other amino acid, (d) S at residue position 143 is replaced by an amino acid other than T, (e) D at residue position 144 is replaced by any other amino acid, (f) G at residue position 145 is replaced by any other amino acid and (g) N at residue position 146 is replaced by any amino acid.

The improved vaccine of the present invention is such that it is capable of forming "neutralizing antibodies", i.e., antibodies that will protect patients against hepatitis B virus. Accordingly, the present invention is also directed to methods for protecting humans against contracting hepatitis B.

The improved vaccines of the present invention can be used to improve immune response and to overcome non-responsiveness to certain known hepatitis B virus vaccines.

The vaccine to be improved upon according to the invention is one which generally has the entire S protein of hepatitis B virus, although it may contain one or more portions thereof. Generally such vaccine is produced by recombinant means.

After ascertaining non-permitted replacements in S(139–147), a mutant would be produced, generally by recombinant means, having the entire S protein of hepatitis B virus with such amino acid replacement. It is also possible that such mutant would have a portion of the entire S protein and may be a peptide. Such mutant may have one or more amino acid replacements within S(139–147). Also, the improved vaccine may contain more than one mutant.

The mutant may be prepared by in vitro mutagenesis, wherein mutations are first generated in cloned segments of DNA by using a variety of chemical and enzymatic methods. These methods can produce mutations at an extremely high frequency (approaching 100% in some cases), and essentially all possible mutations can be generated. Once generated, the mutant DNAs are subject to DNA sequence analysis and then analyzed for the specific function of interest. In this way, mutations can be obtained in a systematic manner without regard to their phenotype. The end result is that the functions of a given region of DNA can be investigated in much more detail.

Five basic protocols can, for example, be used for altering the nucleotide sequence of cloned DNA segments. The first method, oligonucleotide-directed mutagenesis, makes it possible to alter the DNA sequence in a defined way. This is accomplished by synthesizing an oligonucleotide whose sequence contains the mutation of interest, hybridizing the oligonucletoide to a template containing a wild-type sequence, and extending the primer with T4 DNA polymerase. The resulting product is a heteroduplex molecule containing a mismatch due to the mutation in the oligonucleotide. The mutation is "fixed" upon repair of the mismatch in *Escherichia coli* cells. This method is extremely valuable for situations in which it is desired to determine the effects of particular changes in the DNA, and it is also useful for introducing restriction sites at specific positions within a given stretch of DNA. However, it is relatively expensive (one oligonucleotide per mutation) and hence is limited to circumstances where one or few specific mutations are desired.

Another method (second method) for generating a large number of mutations within a small region of DNA makes use of synthetically derived mixtures of oligonucleotides that are obtained by adding small, defined amounts of "incorrect" precursors at each step of the DNA synthesis. Each oligonucleotide molecule in the mixture thus has a defined probability of being altered from the wild-type sequence. This degenerate oligonucleotide mixture is converted to double-stranded DNA whereupon individual oligonucleotide molecules are isolated by molecular cloning. In principle, mutations occur at the frequency that was programmed into the DNA synthesis, and they occur at random positions throughout the region of interest. The major limitation of this method is the size of the oligonucleotide; thus, it is valuable for mutagenizing regions of DNA as large as 80 bases in length. However, it is noted that larger regions can be mutagenized by using a set of contiguous or overlapping olignucleotides that cover the region of interest.

A third method makes it possible to synthesize any desired gene segment by combining long oligonucleotides. The region of interest is subdivided into pairs of long single-stranded oligonucleotides that can be annealed at their 3' ends. These pairs of oligonucleotides are converted into double-stranded DNA suitable for cloning. The final product, a custom-designed gene, is obtained by correctly assembling the double-stranded oligonucleotides. It is possible to generate desired sequences up to 400 bp in a single step, and longer regions can be obtained by combining the products of individual steps. The ability to synthesize long regions of any desired sequence is extremely valuable. For example, the introduction of restriction sites throughout a region greatly facilitates further analysis, and extensive modification of codons throughout a protein-coding sequence may result in an increased production of the protein. The only disadvantage of this procedure is its relative expense. It is most useful for solving a particular problem or for creating a modified gene that is more amenable for further study.

A fourth method makes it possible to generate many mutations within larger regions of DNA (up to 1 to 3 kb). Here,.single-stranded DNA containing theregion of interest is treated with a variety of chemicals. By using an appropriate oligonucleotide primer, the mutated region is copied and then cloned. The mutation frequency can be set by the severity of the chemical treatment, and essentially all possible base substitutions can be obtained. This method is particularly valuable when mutagenizing regions of DNA that are larger than can be accommodated in a single or a few oligonucleotides (for shorter regions, the second method is prefered). However, since there are many possible mutation in such relatively large regions, this method is less useful for saturating a region with mutations. Instead, it is best suited for obtaining mutations that confer phenotypes of interest.

A fifth protocol, linker scanning, involves a method for creating clustered point mutations in a relatively short region (typcially 4 to 10 bp) such that a restriction site is located at the site of mutation. By creating and analyzing a series of linker-scanning mutations throughout a region, it is possible to quickly determine which sequences are functionally important. In addition, the presence of a common restriction site in these mutations allows for the generation of precise deletion or duplication mutations. For an initial functional dissection of a region, linker-scanning mutations have several advantages. Unlike deletion mutations, the changes are highly localized and do not alter any spacing relationships. Compared to point mutations, they are more disruptive and many fewer derivatives are necessary to cover the region; however, they are much less appropriate for analyzing the sequence requirements of a genetic element. Linker-scanning mutations are often used for dissecting transcriptional regulatory signals; they are rarely employed for analyzing protein-coding sequences.

The skilled artisan would know how to conduct such in vitro mutagenesis. In this regard, incorporated by reference herein are the following descriptions of in vitro mutagenesis: *Recombinant DNA. A Short Course*, Ed. J.D. Watson, J. Tooze and D. T. Kurtz, Scientific American Books, W. H. Freeman and Company, Chapter 8, "In Vitro Mutagenesis", pp. 106–116 and *Current Protocols in Molecular Biology*, Vol. 1, Ed. F. M. Ausubel, R. Brent, R. E. Kingston, D. B. Moore, J. G. Siedman, J. A. Smith and K. Struhl, Chapter 8, "Mutagenesis of Cloned DNA", pp. 8.0.1. to 8.4.7.

Alternatively, the insertion methods described in F. Delpeyroux, N. Chenciner, A. Lim, M. Lambert, Y. Malpiece and R. E. Streeck, "Insertions in the Hepatitis B Surface Antigen, Effect on Assembly and Secretion of 22-nm Particles from Mammalian Cells", *J. Mol. Biol.*, (1987), 195, 343–350, F. Dalpeyroux, N. Peillon, B. Blondel, R. Crainic and R. E. Streeck, "Presentation and Immunogenicity of the Hepatitis B Surface Antigen and a Poliovirus Neutralization Antigen on Mixed Empty Envelope Particles", *Journal of Virology*, 62, 1836–1839, (1988), the entire contents of both of which are incorporated by reference herein, can be employed.

If mutant S(139–147) peptides are employed, such peptides can be chemically synthesized by the well known Merrifield solid phase procedure, isolated from natural sources or cloned from DNA. If peptides are utilized, such peptides may be employed with a carrier, e.g., a protein or polysaccharide carrier.

A vaccine according to the present invention may contain an appropriate buffer and may contain an adjuvant, e.g., aluminum hydroxide.

The improved vaccine of the invention can be prepared and used in the same general manner as disclosed in U.S. Pat. No. 4,118,479, the entire contents of which are incorporated by reference herein.

The vaccine can be administered by subcutaneous, intradermal or intramuscular injection. While the preferred route would depend upon the particular vaccine, it is believed that intramuscular injection will be generally suitable. Frequency of administration will vary depending upon the vaccine. Generally speaking, the vaccine will be administered in two doses about one month apart, followed by a booster at six months to one year after primary immunization. The subsequent dose or the booster will depend on the level of antibody in the blood as a result of the initial immunization, and in certain instances may be unnecessary.

The improved hepatitis vaccine of the present invention is recommended for all persons at risk of developing hepatitis B infection and particularly those at especially high risk such as patients and staff on hemodialysis units, medical personnel, person of tropical populations and those visiting the tropics. In the case of tropical population, particularly in Africa, Asia, the Mediterranean region and South America, where high incidence of hepatitis B infections has been consistently observed, the vaccine should be administered sufficiently early in life to prevent acquisition of the chronic carrier state infection which tends to occur in these regions within the first five years of life. In fact, the vaccine is expected to be useful for all persons not already protected against hepatitis B infections as a result of prior immunity, as well as persons previously vaccinated who are likely to be exposed to a variant subtype, against which they do not have immunity.

The invention will now be described with reference to the following non-limiting examples.

EXAMPLE 1

Peptide Synthesis

Forty-one peptides containing the sequences evident from FIG. 1 were synthesized with a tyrosine residue at the C-terminus added to make the labeling of peptides by $^{125}I$ possible. The peptides were synthesized in the form of amides. All peptides were obtained from the Multiple Peptide System, San Diego, Calif. The purity of the peptides was assessed by high performance liquid chromatography (HPLC) using Vydac C-18 columns and an $H_2O$-acetonitrile gradient system containing 0.05% trifluoracetic acid. The purity of most of the peptides was >80%. The purity of peptides 141(R), 142(S), 143(R), 143(K), 143(D), 144(S), 144(R), 145(D), 145(E), 146(A) (for explanation see FIG. 1) was 70–80%. The purity of peptides 140(K), 146(R), 146(K) and 143(M) was 67.6, 68.9, 69.2 and 45.2%, respectively.

EXAMPLE 2

Comparative Antigenicity of Replacement Set Peptides

Wells of 96-well polystryene plates (Removawell, Immunolon II, Dynatech Laboratories, Chantilly, Va.) were coated with HBsAg subtype adw (200 µl; 100 µg/ml in 0.01 M Tris HCl pH 8.8) overnight at 20° C. The wells were then coated with a mixture of bovine serum albumin (BSA) and gelatin (10 and 2.5 mg/ml, respectively) in 0.14 M NaCl, 0.01 M Tris, 0.02% $NaN_3$ (TS). Aliquots of rabbit antiserum to a-synthetic peptide S(135–155), previously shown to recognize HBsAg (A. R. Neurath, S. B. H. Kent and N. Strick, 1982, "Specificity of Antibodies Elicited by a Synthetic Peptide Having a Sequence in Common With a Fragment of a Virus Protein the Hepatitis B Surface Antigen", *Proc. Natl. Acad. Sci. U.S.A.*, 79, 7871–7875), diluted 150-fold in a mixture of fetal bovine serum and goat serum (9:1), containing 0.1% Tween 20, adjusted to pH 8.0 (TSBG) were mixed with graded quantities (4 ng/ml to 200 µg/ml) of synthetic peptides and incubated for 30 minutes at 20° C. The diluted antiserum, without added peptides, and normal rabbit serum served as positive and negative controls, respectively. Aliquots of the diluted rabbit sera with or without the peptides (200 µl) were added to the HBsAg-coated wells. After overnight incubation at 25° C., the plates were washed with 200 µl of TS and $^{125}I$-labeled anti-rabbit IgG (Kirkegaard & Perry Laboratories, Inc., Gaithersburg, Md.; 200,000 cpm diluted 1:1 with TSBG) were added to the wells. After incubation for 2 hours at 37° C., the wells were washed with TS and counted for radioactivity. Radioactivity, corrected for counts corresponding to diluted normal rabbit serum, was plotted against the $log_{10}$ of the concentration of the respective peptides. The 50% inhibition endpoints were calculated as described by Ritchie et al (D. G. Ritchie, J. M. Nickerson and G. M. Fuller, 1983, "Two Simple Programs For the Analysis of Data from Enzyme-Linked Immunosorbent Assays (ELISA) On a Programmable Desk-Top Calculator", p. 577–588. In J. J. Langone and H. Van Vunakis (Eds), *Methods in Enzymology*, Academic Press, New York, U.S.A.).

EXAMPLE 3

Preparation of Human Peripheral Blood Mononuclear Cells

Sixty ml of blood was collected (in heparin containing syringes) from the antecubital vein of individuals who were vaccinated with a recombinant hepatitis B vaccine (RecombiVax HB; Merck, Sharp and Dohme). Mononuclear cells were separated by Ficoll-metrizoate density gradient centrifugation and washed thrice with $Ca^{++}$ and $Mg^{++}$ free Dulbecco Is phosphate buffered saline (D-PBS). Monocytes were isolated by incubating the peripheral blood mononuclear cells (PBMC) at a concentration of $5 \times 10^6$/ml in RPMI medium containing 10% bovine calf serum (BCS, Hyclone-defined/supplemented) in 75 $cm^2$ tissue culture flasks for 2 hours at 37° C. in a 5.5% $CO_2$ incubator. The non-adherent cells were removed by decanting, washed twice in D-PBS and once in RPMI medium containing 10% human AB-positive serum and used for in vitro proliferative assays. Ninety percent of the adherent cells have the morphological characteristics of monocytes or macrophages.

EXAMPLE 4

In Vitro Proliferative Assay Using Human Lymphocytes

Peripheral blood mononuclear cells were cultured in 96 well flat bottom plates at a density of $2.5 \times 10^5$ cells/100 µl per well in RPMI-1640 medium supplemented with 2mM glutamine, 100 units/ml penicillin, 100 µg/ml streptomycin, 50 µg/ml gentamycin and 10% human AB-positive serum. The cultures (100 µl) were stimulated with either RecombiVax HB or synthetic peptides (both at 0.1 and 0.5 µg/well), or with antiidiotype and isotype-matched control antibody (20 and 50 µg/well). Eighteen hours before the end of each culture period the cells were pulsed with 1 µCi/well of tritiated thymidine ($^3$HTdR). The cells were then harvested onto glass fiber filters using an automatic cell harvester. Proliferation, as measured by thymidine incorporation, was determined by liquid scintillation spectroscopy. Results are expressed as mean counts per minute (cpm) for triplicate cultures.

EXAMPLE 5

In Vitro Proliferation Assay Using Purified Mouse Lymph Node T Cells

Balb/c mice were immunized in the hind foot pads, either with 0.5 µg of RecombiVax HB or with HBsAg subtype ayw (Scripps Laboratories), on day 0, 14 and 21. One week after the last injection, the animals were sacrificed and the popliteal lymph nodes were collected. The nodes were teased apart and the dispersed cells were then washed twice in RPMI-1640 medium without any serum supplement and once in RPMI medium containing 10% bovine calf serum. A cell count was made and the cell concentration was adjusted so that T cell enrichment was then done at $1 \times 10^8$ cells/0.6g of packed nylon wool column. The lymph node cells were incubated on the nylon wool column for 45 minutes at 37° C. in a 5.5% $CO_2$ incubator. The non-adherent cells were collected by washing the column with RPMI-1640 medium containing 10% heat-inactivated BCS. The non-adherent cells were adjusted to a concentration of $2.5 \times 10^5$ cells/well. One hundred µl of cells were plated in 96 well flat-bottomed plates along with $5 \times 10^5$ irradiated syngeneic spleen cells as a source of antigen processing cells (APC). Appropriate concentrations of the different stimulators (100 µl/well) were added and the cells cultured for 120 hours in a $CO_2$ incubator. $^3$H-thymidine (1 µCi/well) was added to each well 18 hours before the end of each culture period. Cells were harvested as described above.

EXAMPLE 6

Selection of Pentides for the Replacement Set Analysis

Synthetic peptides derived from the sequence of S-protein and containing the S(139–147) segment were not recognized in solid phase immunoassays by polyclonal and monoclonal anti-HBs antibodies (A. R. Neurath, S. B. H. Kent and N. Strick, 1982, "Specificity of Antibodies Elicited by a Synthetic Peptide Having a Sequence in Common With a Fragment of a Virus Protein the Hepatitis B Surface Antigen", *Proc. Natl. Acad. Sci. U.S.A.*, 79, 7871–7875).

Therefore it could not have been expected that the replacement set peptides would be recognized by these antibodies. For this reason, it was not possible to carry out replacement set analyses in which each of the amino acid residues in the S(139–147) sequence would be replaced by 19 other amino acids using the methodology described by Geysen et al (Geysen, H. M., S. J. Rodda, T. J. Mason, G. Tribbick and P. G. Schoof, 1987, "Strategies for Epitope Analysis Using Peptide Synthesis", *J. Immunol. Methods*, 102, 259–274).

Applicants' preliminary results demonstrated that the parent peptides CTKPSDGNC and CTKPTDGNC corresponding to distinct HBV subtypes (Table I) inhibited the attachment of anti-HBs to HBsAg-coated wells. Therefore, it was decided to use inhibition tests for the replacement set analysis. However, instead of replacing each amino acid residue in the S(139–147) sequence by all of the other 19 amino acids, an approach which would not be economically feasible, the replacement set was limited to selected amino acid substitutions (FIG. 1). The replacement set peptides were selected on the basis of already established amino acid replacements in rare HBV subtypes and variants (Table II) and on the basis of amino acid substitutions in structurally related proteins shown in general to maintain similarity in tertiary structure (FIG. 2; J. L. Risler, M. O. Delorme, H. Delacroix-and A. Henaut, 1988, "Amino Acid Substitutions in Structurally Related Proteins. A Pattern Recognition Approach", *J. Mol. Biol.*, 204, 1019–1029).

EXAMPLE 7

Tolerance of a B-Cell Epitope Encompassing the Seauence S(139–147) to Amino Acid Substitutions The quantity of IgG attached to HBsAg-coated wells under conditions described herein corresponded to about 1,500 counts per minute (cpm) after subtracting nonspecifically attached IgG ($\cong$250 cpm). Twenty-six of the replacement set peptides at a concentration of 200 µl/ml completely inhibited the attachment of anti-HBs to HBsAg-coated wells. The other 15 peptides having the lowest inhibitory activities (FIG. 1) partially inhibited the attachment of anti-HBs to HBsAg. The concentration of the parent peptide CTKPSDGNC at which a 50% inhibition of anti-HBs attachment occurred ($C_{50}$) was $5.6 \times 10^{-8}$ M. Results based on determining $C_{50}$ for each peptide are summarized in FIG. 1. The results indicate that: (1) amino acid replacements at position 141 are not acceptable, since they lead to decreases of antigenicity exceeding two orders of magnitude. This is in agreement with earlier observations (A. R. Neurath, S. B. H. Kent and N. Strick, 1984, "Monoclonal Antibodies to Hepatitis B Surface Antigen (HBsAg) With Anti-a Specificity Recognize a Synthetic Peptide Analogue (S135–155) With Unmodified Lysine (141),*J. Virol. Methods*, 9, 341–346 and A. R. Neurath, N. Strick and W. R. Oleszko, 1981, "Localization of a Hepatitis B Surface Antigen Determinant Deduced From Results of Chemical Modifications,*J. Virol. Methods*, 3, 115–125). (2) The replacement of aspartic acid at position 144 by amino acids lacking a second carboxyl group also leads to drastic decreases of antigenicity. This also agrees with already published data (Neurath et al, *J. Virol. Methods*, 9, 341–346 (1984) and Neurath et al, *J. Virol. Methods*, 3, 115–125, (1981)). (3) Each of the amino acid replacements within the S(139–147) sequence found in HBV variants (Table II) leads to decreased antigenicity, in agreement with the finding that the variant viruses are not recognized by the monoclonal antibody which induced the generation (selection) of these variants and are less reactive in standard immunoassays for HBsAg. Some of these replacements (S→M at position 143) are sufficient to practically eliminate the recognition of the S(139–147) sequence by the anti-HBs used. (4) Amino acid replacements which distinguish human from other mammalian hepadnaviruses (T→L and D→A at positions 140 and 144, respectively; FIG. 1) decrease, but do not abolish the reactivity with anti-HBs. This agrees with the observed immunological crossreactivity between HBsAg, WHsAg and GSHsAg, respectively. (5) Amino acid replacements at residues 140 and 146 appeared to be more acceptable than replacements at other positions.

In summary, results presented in FIG. 1 can be applied to predicting the immunological impact of amino acid replacements within the S(139–147) sequence which have already occurred and were detected or which remain undetected or still may emerge as the result of mutations within the sequence of HBV DNA.

EXAMPLE 8

Tolerance of a T-Cell Epitope Encompassing Residues S(139–147) to Amino Acid Substitutions Determination of the T-cell stimulatory activity of the replacement set peptides for T-cells isolated from Balb/c mice primed with recombinant HBsAg subtype ayr (FIG. 3) and ad (FIG. 4) indicate the following: (1) murine T-cell proliferative responses are strongly influenced by subtype specific amino acid replacements within the S(139– 147) sequence. This is evident from the observation that the peptide CTKPTDGNC having a threonine residue at position 143 and corresponding to the sequence of S-protein subtype ad was much more effective in eliciting proliferation of T-cells from mice immunized with HBsAg ad in comparison with the ay specific peptide having S instead of T at position 143 (FIG. 4). Conversely, the latter peptide was much more effective in eliciting proliferation of T-cells from mice immunized with HBsAg ayr in comparison with the ad-specific peptide having T at position 143 (FIG. 3). (2) The tolerance of T-cell epitopes to amino acid substitution proved to be much more restricted than the tolerance of B-cell epitopes to such substitutions. (3) In addition to a S→T substitution at position 143 in the S(139–147) ay sequence, the most favored replacement corresponded to T→R at position 140 (FIG. 3). (4) In addition to the T od S→replacement at position 143 of the S(139–147) ad sequence, the most tolerated amino acid replacements were T→G, T→A and T→D at position 140, K→G and K→A at position 141 and D→K at position 144 (FIG. 4). (5) In addition to the subtype specific replacement T→S at position 143, T-cell epitopes, similarly as B-cell epitopes, appeared to be most tolerant to substitutions at position 140, although the permitted substitutions at this position were much more restricted for T-cell epitopes than for B-cell epitopes.

The proliferation of T-cells, isolated from humans immunized with a recombinant HBsAg vaccine (Merck Sharp & Dohme), induced by the replacement set peptides suggest a higher degree of tolerance to amino acid substitutions for human T-cell epitopes in comparison with mouse T-cell epitopes (FIG. 5). The subtype specific restriction of T-cell proliferative responses observed with mouse T-cells was not evident for human T-cells, since T-cells from individuals immunized with HBsAg ad responded virtually equally to the heterologous ay-specific S(139–147) peptide as to the homologous peptide (FIG. 5). Some of the replacement set peptides with substitutions at position 140 induced higher proliferative responses in comparison with the parent peptides corresponding to the S(139–147) sequence subtypes ad or ay. These results are in agreement with the observation that replacements at residue 140 are the most tolerated for both B-cell epitopes and T-cell epitopes. At position 141 the replacement of lysine by glutamic acid was not tolerated at all, as evident from the total lack of proliferation of T-cells by the 141(E) peptide in all individuals studied. A similar abrogation of T-cell responses was observed when proline at position 142 was replace by serine, and by all substitutions made at position 146. Some selected replacements at positions 143, 144 and 145 were acceptable, as indicated by the proliferative responses induced by the corresponding peptides. Results in FIG. 5 also indicate that the tolerance of T-cell epitopes of amino acid substitutions differs somewhat in different individuals. The stimulatory activity of the replacement set peptides for T-cells was tested in seven individuals. Overall, the permitted substitutions at all positions were considerably more restricted even for human T-cells when compared to the tolerance of replacements for B cell epitopes.

It will be appreciated that the instant specification is set forth by way of illustration and not limitation, and that various modifications and changes may be made without departing from the spirit and scope of the present invention.

What is claimed is:

1. A vaccine comprising a hepatitis B virus surface antigen having the sequence (CTKPSDGNC) within residues S(139–147) and at least one non-permitted variant of said surface antigen where at least one of the following substitutions in S(139–147) is made:

at 141 K is substituted with D, E or R
at 142 P is substituted with S
at 143 T(S) is substituted with G, D, E, R, K or M
at 144 D is substituted with G, A, S, R, K, T, N or E
at 145 G is substituted with A, S, D, R or K; and
at 146 N is substituted with G, A, S, R, K or D said vaccine being essentially free of permitted variants of hepatitis B virus surface antigen having the sequence (CTKPSDGNC) within residues S(139–147).

2. The vaccine of claim 1 wherein said at least one non-permitted variant of said surface antigen has at least one of the following substitutions in the S(139–147) sequence (CTKPSDGNC):

at 141 K is substituted with E
at 142 P is substituted with S
at 143 T(S) is substituted with M
at 144 D is substituted with N or E
at 145 G is substituted with A or R; and
at 146 N is substituted with D.

* * * * *